(12) United States Patent
Weichenberger et al.

(10) Patent No.: US 11,435,461 B2
(45) Date of Patent: Sep. 6, 2022

(54) METHOD AND SYSTEM TO PREVENT DEPOLING OF ULTRASOUND TRANSDUCER

(71) Applicant: GE Precision Healthcare LLC, Wauwatosa, WI (US)

(72) Inventors: Harald Weichenberger, Oberhofen (AT); Anton Hörl, Strasswalchen (AT); Reinhold Brüstle, Frankenburg (AT); Bruno Hans Haider, Rehoboth Beach, DE (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 183 days.

(21) Appl. No.: 16/516,798

(22) Filed: Jul. 19, 2019

(65) Prior Publication Data

US 2021/0018607 A1  Jan. 21, 2021

(51) Int. Cl.
*G01S 7/52* (2006.01)
*B06B 1/06* (2006.01)
*H01L 41/04* (2006.01)
*H01L 41/08* (2006.01)
*H01L 41/187* (2006.01)
(Continued)

(52) U.S. Cl.
CPC .......... *G01S 7/52096* (2013.01); *A61B 8/14* (2013.01); *A61B 8/4444* (2013.01); *A61B 8/4494* (2013.01); *B06B 1/0215* (2013.01); *B06B 1/0622* (2013.01); *G01S 7/5202* (2013.01); *H01L 41/042* (2013.01); *H01L 41/0825* (2013.01); *H01L 41/1875* (2013.01); *H01L 41/1876* (2013.01); *H01L 41/257* (2013.01); *H01L 41/29* (2013.01); *H01L 41/338* (2013.01); *B06B 2201/40* (2013.01); *B06B 2201/76* (2013.01)

(58) Field of Classification Search
CPC ..... G01S 7/52096; G01S 7/5202; A61B 8/14; A61B 8/4444; B06B 1/0215; B06B 1/0622; B06B 2201/40; B06B 2201/76; H01L 41/042; H01L 41/0825
See application file for complete search history.

(56) References Cited

U.S. PATENT DOCUMENTS 2,166,763 A   7/1939  Mason
4,670,682 A   6/1987  Harnden, Jr. et al.
(Continued)

FOREIGN PATENT DOCUMENTS

WO   2017002007 A1   1/2017

*Primary Examiner* — Isam A Alsomiri
*Assistant Examiner* — Abdallah Abulaban
(74) *Attorney, Agent, or Firm* — The Small Patent Law Group LLC; Dean D. Small

(57) ABSTRACT

An ultrasound system, probe and method are provided. The ultrasound system includes a transducer with piezoelectric transducer elements polarized in a poling direction. A bipolar transmit circuit is configured to generate a transmit signal having first and second polarity segments. The first and second polarity segments have corresponding first and second peak amplitudes. A bias generator is configured to generate a bias signal in a direction of the poling direction. The bias signal is combined with the transmit signal to form a biased transmit signal that is shifted in the direction of the poling direction and still includes both of positive and negative voltages over a transmit cycle.

20 Claims, 12 Drawing Sheets

(51) Int. Cl.
*H01L 41/29* (2013.01)
*H01L 41/338* (2013.01)
*H01L 41/257* (2013.01)
*A61B 8/14* (2006.01)
*A61B 8/00* (2006.01)
*B06B 1/02* (2006.01)

(56) References Cited

U.S. PATENT DOCUMENTS

| | | |
|---|---|---|
| 5,295,487 A | 3/1994 | Saitoh et al. |
| 5,298,828 A | 3/1994 | Radovanovich |
| 5,402,791 A | 4/1995 | Saitoh et al. |
| 5,438,998 A | 8/1995 | Hanafy |
| 5,740,128 A | 4/1998 | Hossack et al. |
| 5,833,361 A | 11/1998 | Averkiou et al. |
| 5,879,303 A | 3/1999 | Averkiou et al. |
| 5,913,823 A | 6/1999 | Hedberg et al. |
| 5,998,910 A | 12/1999 | Park et al. |
| 6,238,481 B1 | 5/2001 | Yamashita et al. |
| 6,241,676 B1 | 6/2001 | Savord |
| 6,497,660 B1 * | 12/2002 | Dillman ............... G01S 7/52025 600/437 |
| 6,532,819 B1 | 3/2003 | Chen et al. |
| 6,666,825 B2 | 12/2003 | Smith et al. |
| 7,078,073 B2 | 7/2006 | Riigney et al. |
| 7,094,444 B2 | 8/2006 | Rigney et al. |
| 7,289,336 B2 | 10/2007 | Burdick, Jr. et al. |
| 7,545,012 B2 | 6/2009 | Smith et al. |
| 7,621,028 B2 | 11/2009 | Gelly et al. |
| 8,659,212 B2 | 2/2014 | Eggen et al. |
| 8,978,216 B2 | 3/2015 | Calisti et al. |
| 9,966,578 B2 | 5/2018 | Stringer et al. |
| 2005/0215909 A1 * | 9/2005 | Barnes ............... G01S 7/52039 600/459 |
| 2018/0156904 A1 * | 6/2018 | Owen ................... A61B 8/485 |

\* cited by examiner

METHOD AND SYSTEM TO PREVENT DEPOLING OF ULTRASOUND TRANSDUCER

FIELD

Aspects of the present disclosure relate to medical imaging. More specifically, certain embodiments relate to methods and systems for preventing depoling of an ultrasound transducer.

BACKGROUND OF THE INVENTION

Single crystal piezoelectric materials may be used to form the acoustical stacks in ultrasound probes. The manufacture of an acoustical stack for use within an ultrasound probe includes stacking or sandwiching the piezoelectric material with other layers of materials such as graphite based materials or heavily loaded epoxy materials that may be used to form matching layers, flex materials with embedded copper traces, and/or other very hard material(s). During manufacture, ultrasound transducers are "poled" to improve the piezoelectric effect. The poling process is done by applying an electric field to the transducer along a predetermined direction relative to a reference axis of the piezoelectric material. The single crystal material and other transducer layers are diced into sub-parts which define separate transducer elements. The transducer elements are attached with electrodes during the assembly process. The electrodes are used to convey transmit signals to the corresponding transducer elements within the piezoelectric material and to collect received signals from the corresponding transducer elements.

During operation, a transmit voltage is applied between the electrodes connected to the piezoelectric material in order to induce an electric field in the transducer. The electric field results in a mechanical dimension change of the transducer element based on the piezoelectric effect. The mechanical dimension change is used to create an acoustic wave which is emitted by the probe. The acoustic wave is partially reflected on different anatomical layers. The reflected wave causes mechanical distortions of transducer elements, during a receive operation. The mechanical distortions during the receive operation induce an electrical signal, due to the piezoelectric effect, within the transducer. The electrodes transfer the electrical signals to the ultrasound console, where the electrical signals are used to create the ultrasound image. Transmit and receive operations are applied to a large number of electrodes and an associated large number of transducer elements.

If unduly high voltages are applied in a direction opposite to the initial poling direction the piezoelectric effect can be degraded. A degradation of this effect leads to lowered sensitivity of the ultrasound probe (also referred to as a depoling effect). The amount of degradation depends on many factors like transducer temperature, pattern of applied voltage signal, ending voltage polarity (positive or negative voltage), material composition of transducer, thickness of transducer et cetera. The depoling effect is a major challenge with single crystal ultrasound probes.

Heretofore, methods have been proposed to attempt to reduce the depoling effect. For example, U.S. Pat. No. 6,497,660, to Dillman et al., proposed to add a large biasing voltage to the transmit voltage signal. Dillman teaches to bias the bipolar voltage signal to maintain a same polarity as the poling direction of the transducer throughout a transmit operation. During the transmit cycle, Dillman's bias generator shifts the bipolar voltage signal such that instead of sitting at 0 Volts in the quiescent state, the bipolar voltage signal sits at least −XV volts. In FIG. 4 Dillman shows a biased bipolar voltage signal that has a quiescent state at −Xv, a peak value of 0 volts and a minimum value of −2XV, such that the biased bipolar voltage signal preferably should not cross 0 Volts. However, in order to maintain Dillman's large biasing voltage, the system must include a high voltage biasing circuit that is expensive and unreliable. Also, applying a large biasing voltage to the probe throughout the transmit cycle can shorten the life of the probe and introduce other circuit complexities.

Additional limitations and disadvantages of conventional and traditional approaches will become apparent to one of skill in the art, through comparison of such systems with some aspects of the present disclosure, as set forth in the remainder of the present application with reference to the drawings.

BRIEF DESCRIPTION

In accordance with embodiments herein, an ultrasound system is provided. The ultrasound system includes a transducer with piezoelectric transducer elements polarized in a poling direction. A transmit circuit is configured to generate a transmit signal having first and second polarity segments. The first and second polarity segments have corresponding first and second peak amplitudes. A bias generator is configured to generate a bias signal in a direction of the poling direction. The bias signal is combined with the transmit signal to form a biased transmit signal that is shifted in the direction of the poling direction and still includes both of positive and negative voltages over a transmit cycle.

Optionally, the piezoelectric transducer elements may be formed from a single crystal material polarized in the poling direction. The single crystal material may represent a binary single crystal material. The bias signal may be a DC voltage that is applied continuously to the probe connector. The bias generator may be configured to generate the bias signal to have a steady-state voltage of between 2.5V and 10V. The bias generator may be configured to generate the bias signal to have a steady-state voltage of 4V to 6V. The bias generator may be configured to generate the bias signal to have a steady-state voltage of up to 15% of at least one of the first or second peak amplitudes of the transmit signal.

Optionally, the transmit signal may include a series of pulses that repeat. The pulses may have a predetermined pulse width to provide an active transmit signal for up to 5% of the transmit cycle. The bias generator may be configured to continuously apply the bias signal during 90% or more of the transmit cycle. The transmit signal may include a series of pulses that repeat, the pulses having a predetermined pulse width to provide an active transmit signal for up to 5% of the transmit cycle, the bias generator configured to continuously apply the bias signal during the transmit cycle.

Optionally, the ultrasound system may include a probe coupled to a distal end of a probe cable. The probe cable may include a probe connector at a proximal end of the probe cable. The probe connector may be configured to be connected to an ultrasound console. The bias generator may be located within the ultrasound console downstream of the transmit circuit and before the probe connector. The ultrasound system may comprise a probe. The bias generator may be located in the probe.

In accordance with embodiments herein, an ultrasound probe is provided. The ultrasound probe includes a transducer with piezoelectric transducer elements polarized in a poling direction. A probe connector and a transmit line extend from the probe connector to the transducer. The transmit line is configured to convey a transmit signal with different pattern. The different pattern segments have corresponding peak amplitudes. A bias generator is coupled to the transmit line. The bias generator is configured to generate a bias signal in a direction of the poling direction. The bias signal is combined with the transmit signal to form a biased transmit signal that is shifted in the direction of the poling direction and still includes both of positive and negative voltages over a transmit cycle. The bias signal may also be active during the receive time.

Optionally, the piezoelectric transducer elements may be formed from a single crystal material polarized in the poling direction. The single crystal material may represent a binary single or ternary crystal material. The bias generator may be configured to generate the bias signal to have a steady-state voltage of between 2.5V and 10V.

In accordance with embodiments herein, a method is provided. The method utilizes a transducer to transmit ultrasound signals and receive echo ultrasound signals from a region of interest. The transducer includes piezoelectric transducer elements polarized in a poling direction. The method generates a transmit signal having several polarity segments. The different polarity segments having corresponding different peak amplitudes. The method generates a bias signal in a direction of the poling direction and combines the bias signal with the transmit signal to form a biased transmit signal that is shifted in the direction of the poling direction and still includes both of positive and negative voltages over a transmit cycle. The bias signal may also be active during the receive time.

Optionally, the method may comprise providing the piezoelectric transducer elements formed from a single crystal material polarized in the poling direction. The method may utilize a binary or ternary single crystal material to form the transducer elements. The method may continuously apply a DC voltage as the bias signal. The method may comprise at least one of: generating the bias signal to have a steady-state voltage of up to 10V; generating the bias signal to have a steady-state voltage of up to 6V; generating the bias signal to have a steady-state voltage of up to 15% of at least one of the first or second peak amplitudes of the transmit signal; or continuously applying the bias signal during 90% or more of the transmit cycle.

DETAILED DESCRIPTION

Figure 1:
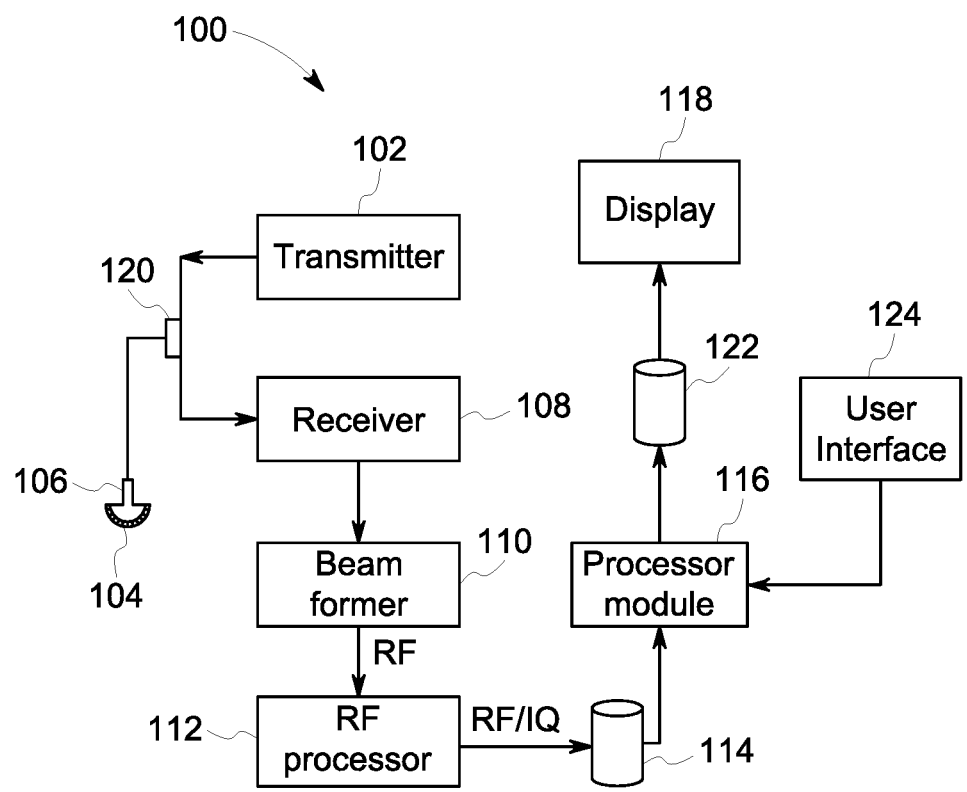
FIG. 1 illustrates an ultrasound system including a transmitter that drives an array of transducer elements within a probe to emit pulsed ultrasonic signals into a body in accordance with embodiments herein.

The foregoing summary, as well as the following detailed description of certain embodiments will be better understood when read in conjunction with the appended drawings. To the extent that the Figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random-access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

The term "sensitivity" shall mean is the ratio of electrical output to signal input or signal output to electrical input Embodiments herein may be implemented in connection with the structure and functions described in one or more of the following published patent applications: U.S. Pat. No. 9,966,578, issued May 8, 2018, entitled "SEAL RING AND ASSOCIATED METHOD"; U.S. Pat. No. 8,978,216, issued Mar. 17, 2015, entitled "METHOD FOR FORMING AN ACOUSTICAL STACK FOR AN ULTRASOUND PROBE"; U.S. Pat. No. 7,621,028, issued Nov. 24, 2009, entitled "METHOD FOR OPTIMIZED DEMATCHING LAYER ASSEMBLY IN AN ULTRASOUND TRANSDUCER"; U.S. Pat. No. 7,545,012, issued Jun. 9, 2009, entitled "CAPACITIVE MICROMACHINED ULTRASOUND TRANSDUCER FABRICATED WITH EPITAXIAL SILICON MEMBRANE"; U.S. Pat. No. 7,289,336, issued Oct. 30, 2007, entitled "ELECTRONIC PACKAGING AND METHOD OF MAKING THE SAME"; U.S. Pat. No. 7,094,444, issued Aug. 22, 2006, entitled "METHOD FOR PREPARING COATED COMPONENTS USING NIAL BOND COATS"; U.S. Pat. No. 7,078,073, issued Jul. 18, 2006, entitled "METHOD FOR REPAIRING COATED COMPONENTS"; U.S. Pat. No. 6,6666,825, issued Dec. 23, 2003, entitled "ULTRASOUND TRANSDUCER FOR IMPROVING RESOLUTION IN IMAGING SYSTEM". The complete subject matter of the published patents, patent applications and other publications referenced above, and hereafter, are expressly incorporated herein by reference in their entirety.

Embodiments herein may be implemented in connection with a variety of ultrasound transducers without limitation on a geometry of the transducer. However, implementations herein may have better suitability in connection with transducers that are made from materials susceptible to depoling, including (but not limited to) single crystal materials and the like. In particular, embodiments herein are well-suited to limit or eliminate the depoling effect in transducer elements that are constructed substantially from binary single crystal materials or having a substantially homogeneous composition of binary single crystal materials. In particular, embodiments herein utilize low voltage bias signals to stabilize weaker binary single crystal materials when utilizing bias signals having lower voltage, as compared to the voltage levels of bias signals used with ternary single crystal materials.

Embodiments may be implemented in connection with ultrasound probes having various types and arrangements of transducers that are configured to collect any and all types of ultrasound data sets, including (but not limited to) B-mode data, power Doppler data, Doppler data, strain data, two-dimensional data, three-dimensional data, four dimensional data, shear wave data or otherwise, as described herein and as described in the patents, patent applications and other publications referenced and incorporated herein.

While the primary embodiments are described in connection with ultrasound transducers utilized in connection with diagnostic imaging, it is recognized that embodiments may be implemented in connection with ultrasound transducers utilized for other applications. Nonlimiting examples of other applications for ultrasound transducers include ultrasound therapy systems (e.g., ultrasound based treatment of tumors, ultrasound based removal of fat tissue), opto-acoustic ultrasound, sonar, ultrasound based inspection of mechanical structures, ultrasound based inspection of mechanical connections (e.g., welds and other bonded interfaces) and the like. Traditionally, transducers for therapy, sonar and inspection applications have utilized different crystal structures that were less susceptible to depoling (e.g., not single crystal materials), and thus were not able to take advantage of other benefits offered by single crystal structures. For example, the higher voltages utilized in connection with therapy, sonar and inspection applications may otherwise accelerate the depoling process and the degradation of the transducer, thereby rendering single crystal structures unsuited for such applications. However, with the addition of the improvements described herein, depoling is avoided, even at higher transmit voltages, thereby allowing single crystal transducers to be used in higher voltage applications.

FIG. 1 illustrates an ultrasound system 100 including a transmitter 102 that drives an array of transducer elements 104 (e.g., piezoelectric elements) within a probe 106 to emit pulsed ultrasonic signals into a body. The elements 104 may comprise a single crystal material as discussed herein. The elements 104 may be arranged, for example, in one or two dimensions. A variety of geometries may be used, and the probe 106 may be capable of acquiring one, two, three and/or four-dimensional image data. The system 100 may have a probe port 120 for connecting the probe 106 or the probe 106 may be hardwired to the system 100.

The transmitter and the ultrasound probe may be implemented and/or configured for one-dimensional (1D), two-dimensional (2D), three-dimensional (3D), and/or four-dimensional (4D) ultrasound scanning. The ultrasound probe may comprise a one-dimensional (1D, 1.25D, 1.5D or 1.75D) array or a two-dimensional (2D) array of piezoelectric elements. The ultrasound probe may comprise a group of transmit transducer elements and a group of receive transducer elements, that normally constitute the same elements. The transmitter may be driven by the transmit beamformer. The transmit beamformer may comprise suitable circuitry that may be operable to control the transmitter which, through a transmit sub-aperture beamformer, drives the group of transmit transducer elements to emit ultrasonic transmit signals into a region of interest (e.g., human, animal, underground cavity, physical structure and the like). In this regard, the group of transmit transducer elements can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The ultrasonic signals are back scattered from structures in the body, like fatty tissue or muscular tissue, to produce echoes that return to the elements 104. The echoes are received by a receiver 108. The received echoes are passed through a beamformer 110 that performs beamforming and outputs a radiofrequency (RF) signal. The RF signal then passes through an RF processor 112. Alternatively, the RF processor 112 may include a complex demodulator (not shown) that demodulates the RF signal to form in-phase and quadrature (IQ) data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 or memory 122 during a scanning session and then processed and displayed in an off-line operation.

A user interface 124 may be used to input data to the system 100, adjust settings, and control the operation of the processor module 116. The user interface 124 may have a keyboard, trackball and/or mouse, and a number of knobs, switches or other input devices such as a touchscreen. The display 118 includes one or more monitors that present patient information, including diagnostic ultrasound images to the user for diagnosis and analysis. One or both of memory 114 and memory 122 may store two-dimensional (2D) and/or three-dimensional (3D) datasets of the ultrasound data, where such datasets are accessed to present 2D and/or 3D images. Multiple consecutive 3D datasets may also be acquired and stored over time, such as to provide real-time 3D or four-dimensional (4D) display. The images may be modified and the display settings of the display 118 also manually adjusted using the user interface 124.

Figure 2:
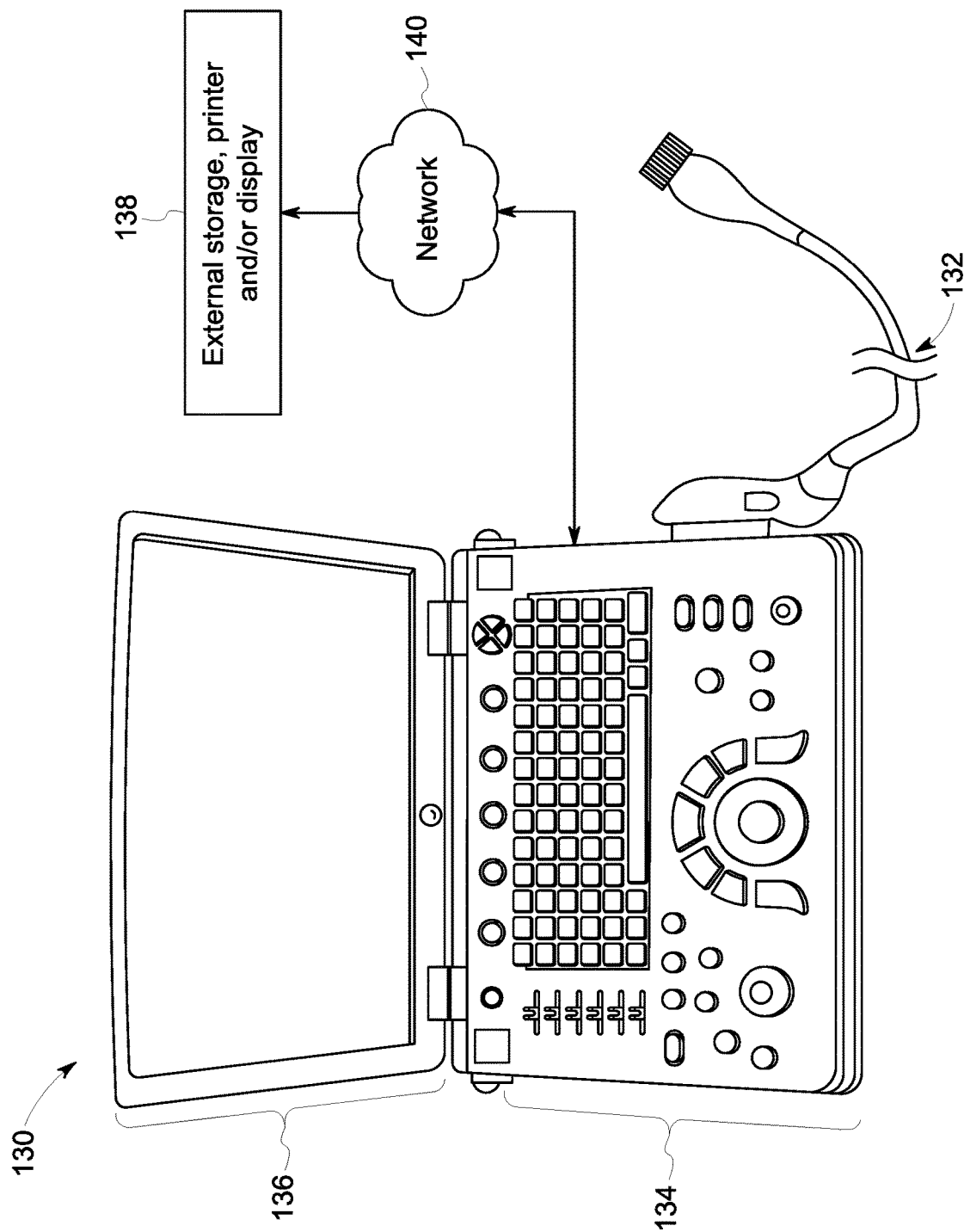
FIG. 2 illustrates a 3D-capable miniaturized ultrasound system having a probe that may comprise elements having single crystal material and/or single crystal composite material in accordance with embodiments herein.

FIG. 2 illustrates a 3D-capable miniaturized ultrasound system 130 having a probe 132 that may comprise elements 104 having single crystal material as discussed herein. The probe 132 may be configured to acquire 3D ultrasonic data. For example, the probe 132 may have a 2D array of transducer elements 104. A user interface 134 (that may also include an integrated display 136) is provided to receive commands from an operator.

As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136. It should be noted that the various embodiments may be implemented in connection with a miniaturized ultrasound system having different dimensions, weights, and power consumption.

Figure 3:
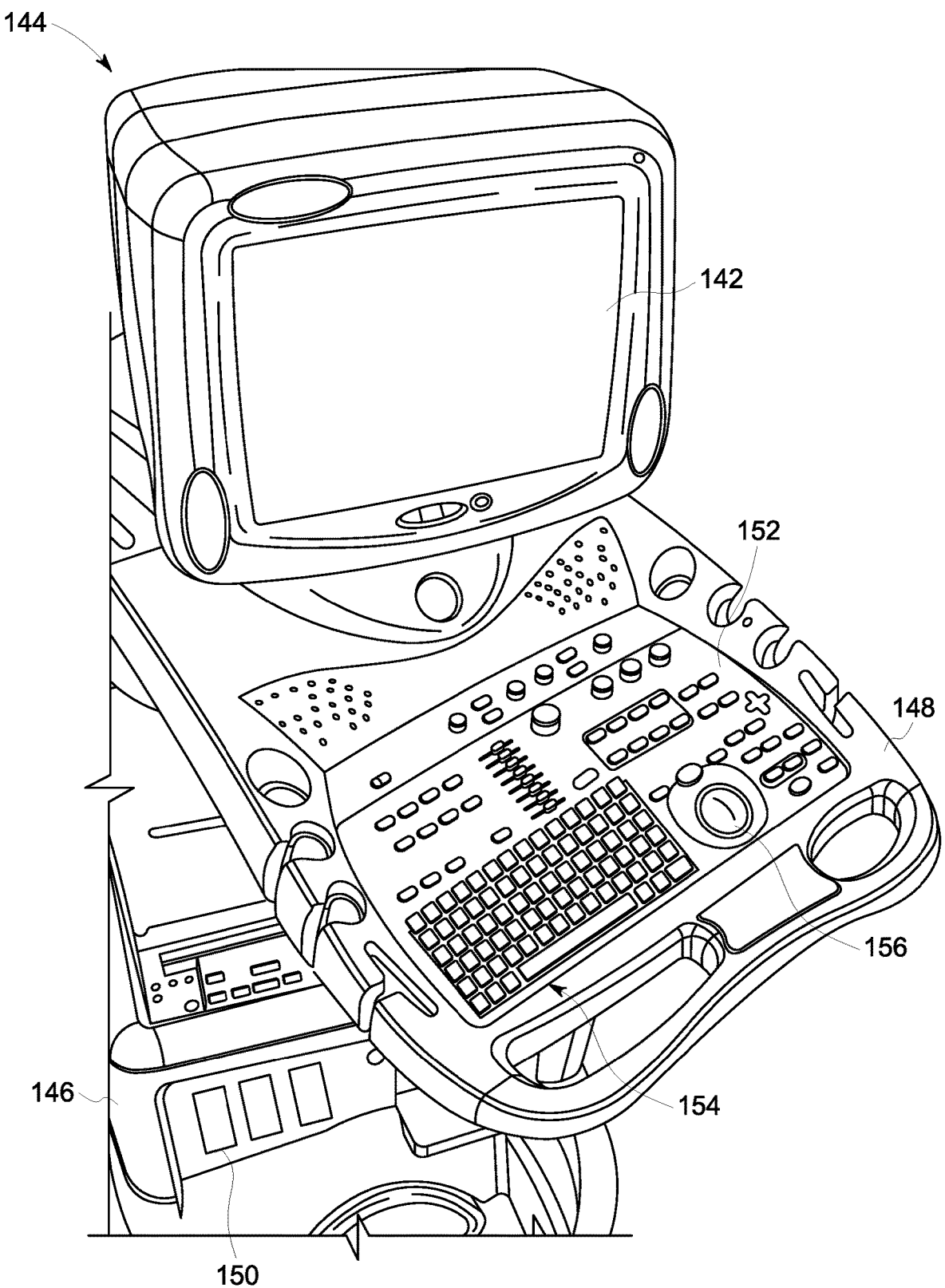
FIG. 3 illustrates a mobile ultrasound imaging system provided on a movable base in accordance with embodiments herein.

FIG. 3 illustrates a mobile ultrasound imaging system 144 provided on a movable base 146. The ultrasound imaging system 144 may also be referred to as a cart-based system. A display 142 and user interface 148 are provided and it should be understood that the display 142 may be separate or separable from the user interface 148. The system 144 has at least one probe port 150 for accepting probes (not shown) that may have elements 104 that comprise single crystal material as discussed herein.

The user interface 148 may optionally be a touchscreen, allowing the operator to select options by touching displayed graphics, icons, and the like. The user interface 148 also includes control buttons 152 that may be used to control the system 144 as desired or needed, and/or as typically provided. The user interface 148 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided.

Figure 4:
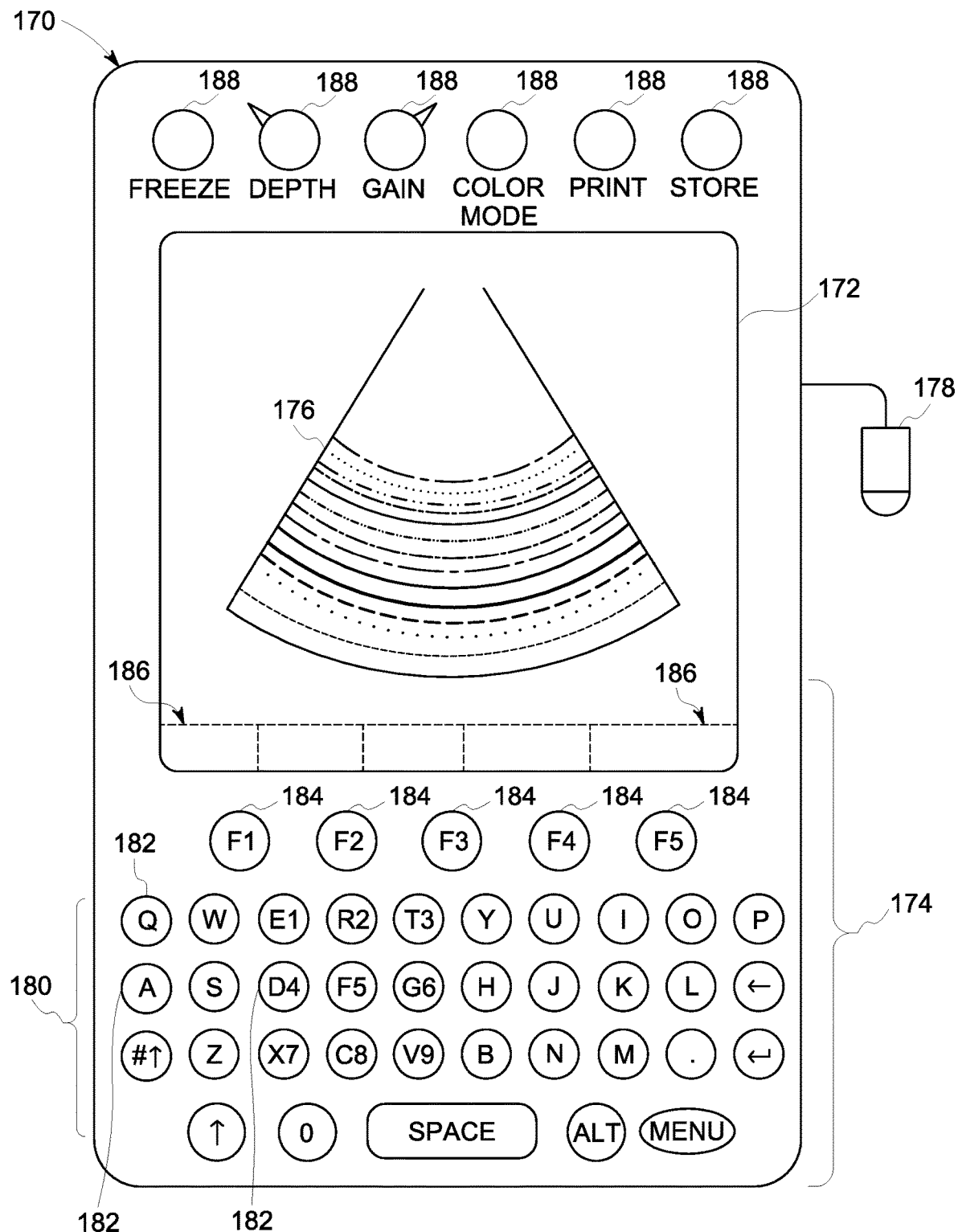
FIG. 4 illustrates a hand carried or pocket-sized ultrasound imaging system wherein display, and user interface form a single unit in accordance with embodiments herein.

FIG. 4 illustrates a hand carried or pocket-sized ultrasound imaging system 170 wherein display 172 and user interface 174 form a single unit. By way of example, the pocket-sized ultrasound imaging system 170 may be approximately 2 inches wide, approximately 4 inches in length, and approximately 0.5 inches in depth and weighs less than 3 ounces. The display 172 may be, for example, a 320×320 pixel color LCD display (on which a medical image 176 may be displayed). A typewriter-like keyboard 180 of buttons 182 may optionally be included in the user interface 174. The system 170 is connected to a probe 178 that has transducer elements 104 comprising a single crystal material as discussed herein. Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 172. The system 170 may also have additional keys and/or controls 188 for special purpose functions, which may include, but are not limited to "freeze," "depth control," "gain control," "color-mode," "print," and "store."

The term acoustical stack may be used herein to refer to several layers that are attached together in a stacked configuration. Each of the elements 104 (shown in FIG. 1) within the probe 106 comprises an acoustical stack. In one embodiment, the acoustical stack includes a piezoelectric layer that is formed of a piezoelectric material such as single crystal piezoelectric material. The piezoelectric layer may have, for example, a thickness of approximately ½ or ¼ of λ, wherein λ is the wavelength of sound in the piezoelectric material for the desired center frequency of the useful bandwidth. Electrodes may be formed with a thin metallic layer and deposited on at least top and bottom sides of the piezoelectric material.

Figure 5:
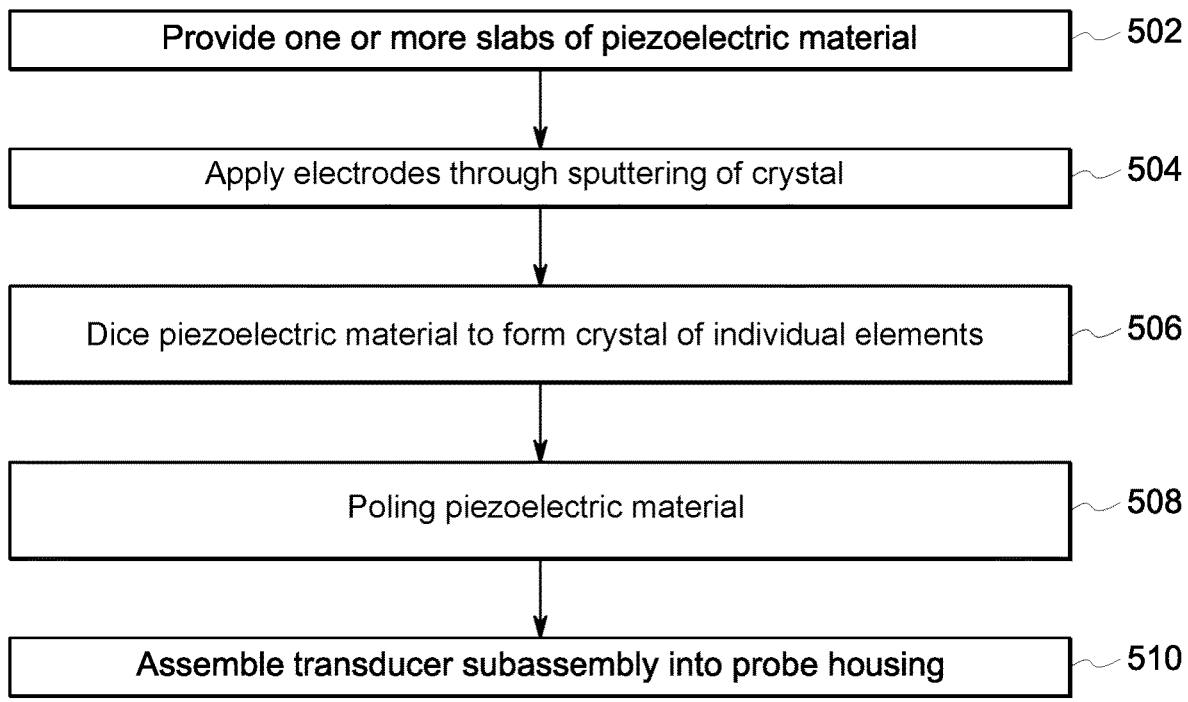
FIG. 5 illustrates a method for manufacturing a transducer array in accordance with embodiments herein.

FIG. 5 illustrates a method for manufacturing a transducer array in accordance with embodiments herein. At 502, a slab of a piezoelectric material is provided. The slab of piezoelectric material may also be referred to as a piezoelectric substrate, which may be formed form different types of piezoelectric compounds. Typically, the piezo-material is fully metallized on the outside surface. The metallization forms the individual element electrodes after dicing the acoustic stack into individual elements. In accordance with at least some embodiments, the substrate may be formed as a single crystal material. While the single crystal material may be a binary or ternary single crystal material, more preferably, the single crystal material is a binary single crystal material. Non-limiting examples of single crystal materials that may be utilized include bi-composites such as lead zirconium niobate-lead titanate (PZN-PT) and lead magnesium niobate-lead titanate (PMN-PT). PMN-PT has an internal structure that induce different but specific characteristics. PMN-PT exhibits piezoelectric properties and is composed of two different groups of atoms that behave as a unit, each an oxide, called radicals (e.g., Pb(Mg1/3 Nb2/3)O3 and PbTiO3). PMN-PT is part of the relaxor-ferroelectric material class, and has a monocrystalline structure, unlike commonly used piezoelectric materials that have a granular piezoceramic structure. This means that defects and grain boundaries are absent and thus PMN-PT can be machined to a more precise degree, with optical grade finish. Other properties that differentiate PMN-PT from granular piezoelectric materials, such as PZT, are also directly linked to the monocrystalline structure. Such properties are optical, mechanical or electrical and can be anisotropic (directly dependent). Another advantage of PMN-PT having a monocrystalline structure is its uniformity, ensuring consistent values for the piezoelectric coefficients.

The piezoelectric substrate includes a proximal or front surface and a distal or back surface. Once the substrate is assembled into an ultrasound probe, during operation of the probe, the probe is positioned against a region of interest and ultrasound waves are transmitted in a scanning direction into the ROI. Structures within the ROI signals in response to the transmitted ultrasound waves. In medical imaging and therapy applications, the probe is held against tissue for an ROI, with the front face of the probe generally oriented perpendicular to the scanning direction. In non-destructive testing, the probe is held against a structure that includes an ROI with the scanning direction extending into the ROI. In sonar applications, the probe is located within a fluid (e.g., ocean). The proximal surface is the surface of the substrate located closest to (or against) the tissue, structure or fluid containing the ROI with the scanning direction extending into the ROI.

In accordance with some probe designs, the proximal and distal surfaces of the substrate may extend along generally parallel planes (e.g., for linear transducer configurations). Optionally, the proximal and distal surfaces may extend along generally concentric arcs (e.g., for curved transducer configurations). Optionally, the proximal and/or distal surfaces may be constructed to extend along other paths that are not planar and/or do not have a constant curve. For example, at least the proximal surface may extend in a planar manner in a first direction (e.g., longitudinal direction), but extend along a curved path in an orthogonal second direction (e.g., transverse direction). The proximal and distal surfaces of the substrate are spaced apart from one another by a depth or thickness of the substrate as measured along a depth direction. In generally, the proximal and distal surfaces of the substrate may be oriented generally parallel to one another, although in certain embodiments, the proximal and distal surfaces may be oriented at a non-parallel angle to one another.

At 504, an electrode array is sputtered on the piezo material before the part is laminated into the stack. For example, at least the proximal and distal surfaces of the piezoelectric material may be coated with a layer of a conductive material such as gold, nickel, a combination of conductive materials, and the like. Isolation scribings may be made on the proximal and distal surfaces of the crystal to define signal areas and ground areas.

It should be understood that other methods may be used to form electrodes and/or define signal and ground areas. For example, high frequency arrays may be formed with elements that are defined by pre-shaped electrodes on piezo-materials. In the foregoing example, no dicing operation is performed. For example, dicing may be avoided in high frequency arrays where a dicing cut of, for example 30 um width, would take too much of the pitch in the material and is thus technically not feasible. Optionally, at least one matching layer may be fixed, such as by using an adhesive, glue or other material, to the side of the crystal that does not have the isolation scribings. A flex circuit is sandwiched or layered within the acoustical stack to interconnect the stack with the system 100. The flex circuit has a flex insulation layer that may be formed of a material such as Kapton, which is a polyimide film. Other materials may be used. Upper traces are formed on one side of the flex insulation layer and lower traces are formed on the other side of the flex insulation layer. In one embodiment the upper and lower traces may be copper or another metallic material or combination of materials, and may be printed on the flex insulation layer using printing methods known in the art.

At 506, the substrate of piezoelectric material is diced using dicing parameters or conditions. For example, the dicing operation may fully dice through all acoustic layers, such as to dice through all electrically conductive layers to separate all acoustic elements and allow for individual electrical connections. Additionally, elements may be sub-diced to achieve special aspect ratios and preferable vibration modes. Sub-dicing, however, still maintains electric connection for element sub-parts. Optionally, the dicing operation may be limited to partly or partially dicing the substrate material(s) partway through, such that the substrate material is maintained as a slab rather than individual pieces. Optionally, the dicing parameters or conditions may be based on the mechanical properties and geometry of single crystal. Dicing parameters may include, but are not limited to, blade material, spindle speed of rotation, feeding speed and the like. Therefore, the quality of the single crystal is maintained while avoiding the cracking and degrading experienced when using dicing conditions that are needed when dicing an entire acoustical stack. The process for manufacturing the acoustic stack introduces stresses, both in ceramics and single crystal materials. Typically, an annealing step is performed to stress relieve the materials before poling the elements.

In another embodiment, laser cutting, ion milling, chemical etching, wire dicing, plasma, and/or other processes or methods may be used and may be optimized based on the single crystal material. In one embodiment the slab of single crystal material may be a single piece of material, and in another embodiment the slab of single crystal material may be a stack of two or more slabs of single crystal material. Generally, the dicing operation cuts fully through the layers to separate the electrical connections. The dicing operation creates single crystal pieces, each of which corresponds to a single element in the probe. A kerf may extend from the proximal or front surface of the slab through the single crystal material. In one embodiment, the kerf may be a separation, that is, the kerf may completely separate the single crystal pieces. The kerf has a width corresponding to the width of the first dicing. The kerfs are filled with a kerf filling material. The kerf filling material may be a silicon material, organic polymer, epoxy based material, or other material that is suitable for both filling the kerf and suitable for the subsequent dicing operation that will dice the acoustical stack.

At 508, the piezoelectric substrate is "poled" by applying an electric field to the piezoelectric substrate along a predetermined direction. Prior to the poling operation, the piezoelectric substrate exhibits a non-polarized state formed from electric dipoles that are at least partially randomly oriented. When in the non-polarized state, the substrate exhibits a relatively weaker piezoelectric sensitivity as compared to after poling. The poling operation orients the electrical dipoles within the substrate in a common direction referred to as a "poling direction". The polarization of the piezo material is in a transmit direction, that is in the vertical direction of the acoustic stack. The vertical direction extends in a radial direction for a curved probe, and in a longitudinal for a linear or phased probe.

By way of example, one or an array of proximal electrodes may be connected at or near the proximal surface of the substrate with the electrodes arranged in a pattern corresponding to a pattern of transducer elements to be utilized by the probe. The distal surface of the substrate may be connected to a similar array of distal electrodes, fewer electrodes and/or a common electrode. A voltage potential is applied across the proximal and distal electrodes to form the electric field. The electric field is applied with sufficient strength to reorient the electrical dipoles within the piezoelectric substrate to be aligned along a common direction, namely aligned along the scanning direction. For linear probes, the scanning direction extends generally parallel to the depth axis and perpendicular to the face of the probe. For curved probes, in connection with a single transmit operation, the scanning direction extends parallel to a local depth axis (proximate to a transmit axis) and perpendicular to a local region of the probe proximate to the transmit axis.

The poling direction (and orientation of the dipoles) generally extends in a direction between the electrodes coupled to the transducer elements. The electrodes may be positioned on front/proximal and rear/distal surfaces of the transducer elements (or stack). Therefore, the poling direction extends parallel to the depth axis of the stack of the transducer elements. As another example, the transducer elements are arranged in an array in the probe where the probe has a front/proximal surface configured to be positioned proximate to a region of interest. The front surface of the probe extends along a plane. The poling direction generally extends perpendicular to the plane of the front surface of the probe and array of transducer elements.

At 510, the transducer subassembly is assembled into a probe housing, along with any other electrical or mechanical components appropriate to fully assemble an ultrasound probe. Next, the discussion turns to methods and systems to manage operation of an ultrasound probe to limit or eliminate depoling of the piezoelectric material in accordance with embodiments herein. During operation, a transmit voltage is applied to the probe, which leads to an electric field in the transducer. The electric field results in a mechanical dimension change of the transducer element based on the piezoelectric effect. The mechanical dimension change is used to create an acoustic wave which is emitted by the probe. The acoustic wave is partially reflected at different anatomical layers within a region of interest. The reflected waves impact the transducers and cause mechanical distortions of transducer elements. The mechanical distortions create an electric field across the corresponding transducer element, again based on the piezoelectric effect. The electric field within an individual transducer element creates an electrical potential between the electrodes connected to the corresponding transducer element. The electrical potential is sensed as raw receive ultrasound signals and processed to form ultrasound data and ultrasound images.

If unduly high voltages are applied to the transducer elements in a direction opposite to the poling direction, the high voltages degrade the piezoelectric effect exhibited by the transducer elements. For example, the high voltages reorient at least a portion of the electrical dipoles within the composition of the transducer elements, thereby reintroducing at least a partial non-polarization state to the composition of the transducer elements. The degradation in the polarization of the transducer elements reduces the piezoelectric effect exhibited by the transducer elements which leads to lowered sensitivity of the ultrasound probe. The amount of depoling, or degradation in the piezoelectric effect, for a particular probe will depend on various factors, such as voltage amplitude, transducer temperature and/or a signal pattern applied in connection with transmit signals. Complex voltage signal patterns applied during the transmit signals may become more relevant to potential depoling. For example, some voltage signal patterns may have segments with an increased amount of time and/or voltage level that is opposite to the poling direction. The potential for depoling increases as the number or length of segments increases that are opposite to the poling direction.

When simpler transmit signals are utilized, the amount of depoling and degradation may depend on an ending voltage polarity of each transmit signal (e.g., positive or negative voltage) with respect to the polarization direction. For example, an ending of voltage polarity that corresponds to the polarity of the poling direction would have little or no depoling affect, whereas an ending voltage polarity that is opposite to the polarity of the poling direction may have a limited depoling effect.

The negative effects associated with the depoling represent a substantial challenge in connection with newer types of probe designs, and in particular in connection with ultrasound probes utilizing single crystal materials for the transducer arrays. During extensive analysis inventors of the present application observed that depoling could be substantially eliminated in at least certain crystal materials when a "low" level DC bias voltage was applied to the transducer elements during at least transmit operations. The level of the DC bias voltage was defined in terms of a ratio or relation to the voltage applied during transmit operations. In accordance with at least certain embodiments, the low-level DC bias voltage was maintained at or below 15% of the peak voltage applied during a transmit operation. For example, when the transmit voltage is varied between +/−60 V, the DC bias voltage was maintained at or below +/−6 V. By maintaining the DC bias voltage as a small percentage of the transmit voltage, embodiments herein stabilize the electrical dipole orientation of the composition within the transducer elements and thus avoid (or at least substantially diminish) depoling effects.

Further, it was found that, if the DC bias voltage is present for a long period of time within a transmit and receive cycle compared to a length of the transmit voltage pulse, the low-level DC bias voltage stabilized the electrical dipole orientation of the composition within the transducer elements. For example, the DC bias voltage may be maintained continuously throughout an entire transmit and receive cycle and/or maintained for a substantial majority of the transmit and receive cycle (e.g., 90% or more). By way of example, the transmit signal may include a series of pulses that repeat, where the pulses have a predetermined pulse width to provide an active transmit signal for up to 5% of a complete transmit and receive cycle. As a further example, in connection with a B-mode imaging procedure, the imaging sequence (transmit and receive cycle) may include a series of transmit pulses that repeat every 200 μs, where each individual pulse width ranges between 200 and 500 ns, thereby providing an active transmit signal for approximately 5% of the time over the course of an entire transmit operation. The DC bias voltage may be continuously applied during the entire transmit cycle and/or maintained for 90% or more of the transmit cycle.

Optionally, the duty cycle for the DC bias voltage may be varied based on the type of imaging operation and the corresponding type of transmit signal. For example, during a pulse wave Doppler imaging mode, the transmit signal will exhibit a different shape, pulse width and duty cycle, as compared to the transmit signal associated with B-mode imaging. Similarly, the DC bias voltage applied during pulse wave Doppler imaging may be varied. By utilizing a DC bias voltage set to a low percentage of the maximum transmit voltage and by maintaining the DC bias voltage for a substantially longer period of time relative to the pulse width of transmit pulses, it was found that embodiments herein were able to disproportionately increases a maximum transmit voltage for different transducer materials. The disproportionate increase in maximum transmit voltage was able to be sustained without experiencing depoling effect degradation or a decrease in sensitivity. The disproportionate increase in maximum transmit voltage is relative to conventional approaches that utilize no DC bias voltage and relative to conventional approaches that utilize a significantly high DC bias voltage substantially corresponding to the maximum transmit voltage (e.g., such as described by Dillman et al.). Therefore, in accordance with embodiments herein, a voltage of only a few volts can lead to a significant increase of the possible transmit voltage (several tens of volts). At least one benefit of the embodiments herein is, that low voltages lead to a significant improvement if the voltage is applied for a long time compared to transmit voltage signal length and at the same time provide a much simpler and cost-effective solution by utilizing a low voltage DC bias circuit.

By substantially eliminating the effects of depoling, embodiments herein provide probes that are capable of operating transducers with higher voltages, as compared to conventional probes, which thereby increases image quality. Additionally, by substantially eliminating the effects of depoling, embodiments herein provide probes that are capable of using transmit patterns which provide better image quality, where such transmit patterns could not be used in the past because of depoling effects. Further, embodiments herein may be implemented as retrofit solutions to be backward compatible with existing probes, such as through a design change that is applied at a console of the ultrasound imaging system. By applying a retrofit solution, embodiments improve performance of existing products in the installed base.

Figure 6A:
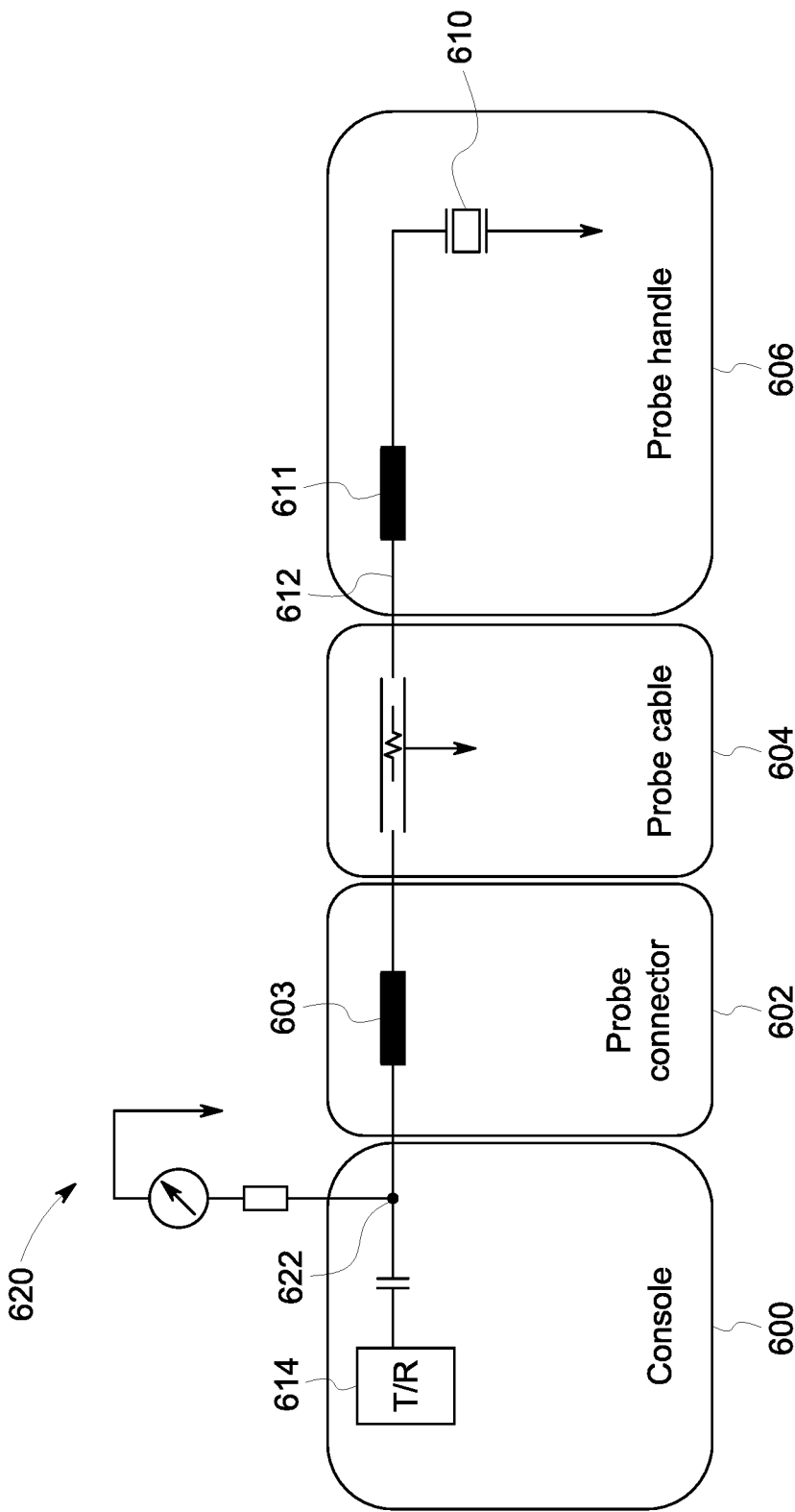
FIG. 6A illustrates a block diagram of an ultrasound system including a DC bias circuit implemented in accordance with embodiments herein.

FIG. 6A illustrates a block diagram of an ultrasound system including a DC bias circuit implemented in accordance with embodiments herein. The ultrasound system includes a console 600 that is connected to a probe connector 602. The console 600 may include all or a portion of the components described and illustrated in connection with one or more of FIGS. 1-4. The probe connector 602 is provided on a proximal end of a probe cable 604. A distal end of the probe cable 604 is connected to a probe 606. A transmit line 612 electrically connects a transducer element 610 to corresponding contacts (not shown) in the probe connector 602. The probe connector 602 is configured to be mated with a mating connector provided on the console (not shown). An inductor 611, within the probe 606, and an inductor 603, within the probe connector 602, are provided along line 612. The probe cable 604 is connected at the probe connector 602 to a transmit/receive (T/R) circuit 614 within the console 600. In the example of FIG. 6A, the transmit line 612 may also be utilized as a receiver line to convey receive signals from the transducer element to the transceiver 614. Optionally, separate transmit and receive lines may be utilized. A capacitor is provided between the T/R circuit 614 and the node 622.

During transmit operations, the T/R circuit 614 delivers a transmit signal to cause the transducer element 610 to transmit ultrasound signals. During receive operations, the T/R circuit 614 records return "echo" signals along line 612 corresponding to ultrasound echo waves sensed at the transducer element 610. A biasing circuit 620 is connected at node 622 within the console 600. The biasing circuit 620 is configured to introduce a bias signal, such as a DC bias voltage, onto the line 612. The bias signal is superimposed at node 622 onto the transmit signal generated by the transmit/receive circuit 614.

FIG. 6A illustrates a simplified diagram associated with a single transducer element 610, although it is understood that the probe 606 will include a transducer array with multiple transducer elements, multiple lines and T/R circuits associated therewith. In accordance with embodiments herein, a common biasing circuit 620 may generate and apply a common bias signal to each line 612 and corresponding transducer element 610. Optionally, multiple biasing circuits 620 may be utilized to generate and apply corresponding bias signals to lines 612 and corresponding transducer elements 610. When multiple biasing circuits 620 are used, the biasing circuits 620 may separately generate bias signals having a common shape, amplitude and duration. Optionally, when multiple biasing circuits 620 are used, the biasing circuits 620 may separately generate bias signals that differ from one another in one or more of shape, amplitude and/or duration. Additionally or alternatively, it may be desirable to apply different bias signals to different sections of a transducer array, such as when the different sections of the transducer array have different shapes and/or receive different transmit signals.

The configuration of FIG. 6A allows a combination of bias circuits 620 to be implemented within the ultrasound system, without any modification to existing ultrasound probes.

Figure 6B:
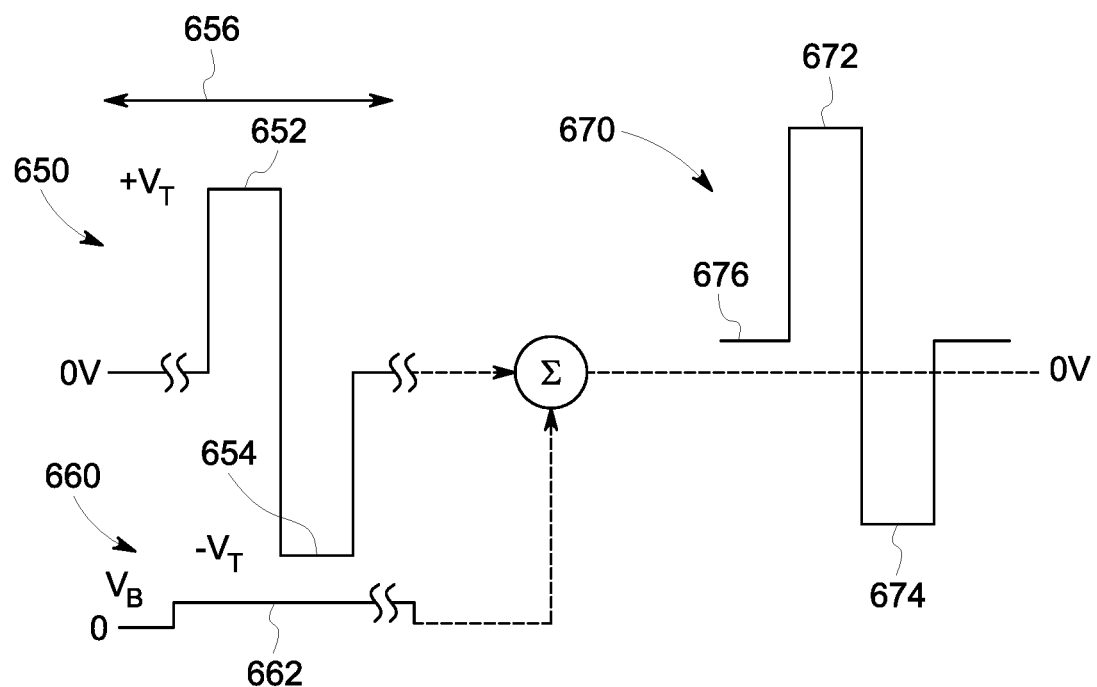
FIG. 6B illustrates an example of a transmit that may be transmitted during one transmit cycle in accordance with embodiments herein.

FIG. 6B illustrates an example of a transmit signal 650 that may be transmitted during one transmit cycle. The transmit signal 650 includes a first polarity segment 652 and a second polarity segment 654. The first and second polarity segments 652, 654 may include one or more pulses and/or may be interleaved with one another. For example, the transmit signal 650 may include a complex combination of positive and negative voltage pulses and/or waveform steps having different amplitudes. The first polarity segment 652 may be in the poling direction, while the second polarity segment 654 is in the opposite or depoling direction. Alternatively, the first polarity segment 652 may be in the depoling direction, while the second polarity segment 654 is in the poling direction. The term polarity segment is used generally to refer collectively to any/all portions of the transmit signal 650 during a transmit cycle that have a common polarity. In the present example, the first polarity segment 652 collectively refers to any and all portions of the transmit signal 650 during a transmit cycle that have a positive polarity, while the second polarity segment 654 collectively refers to any/all portions of the transmit signal 650 during a transmit cycle that have a negative voltage.

The transmit signal 650 in FIG. 6B represents a very simplified waveform that includes a single positive pulse in the first polarity segment 652 and a single negative pulse in the second polarity segment 654, that have peak voltages $+/-V_T$ (e.g., $+/-60$ V). The transmit signal 650 has a peak to peak range corresponding to the sum of the positive and negative peak voltages. The transmit and receive length 656 is substantially longer than the durations of the positive and negative pulses 652 and 654. For example, the transmit and receive time may have a period with a duration of 200 µs, whereas the positive and/or negative pulses have pulse widths of between 200 and 500 ns. The receive time is the time between two transmit signals where no voltage signals are sent to the probe. During the receive time the ultrasound system collects receive data (echoes) from the probe.

In accordance with embodiments herein, a bias signal 660 is generated (e.g., at the biasing circuit 620) that has a polarity that is the same as, and in a common direction with, the poling direction. For example, when the poling direction is positive, the bias signal will have a positive amplitude. Alternatively, when the poling direction is negative, the bias signal has a negative amplitude. The bias signal 660 has a constant bias amplitude $V_B$ that is limited to a relatively small percentage of the peak positive or peak negative pulse amplitude of the transmit signal. By way of example, the amplitude $V_B$ of the bias signal 660 may be less than 15% of the positive peak amplitude of the transmit signal (e.g., 1-6 V). Optionally, the amplitude $V_B$ of the bias signal 660 may be defined based on the "peak to peak" voltage range exhibited by the transmit signal 650. For example, the transmit signal 650 may include a positive peak amplitude +60 V and a negative peak amplitude of −60 V, thereby defining a peak to peak voltage range of 120 V. When defining the amplitude of the bias signal 660 in terms of the peak to peak amplitude, the bias signal amplitude may be an even smaller percentage, such as less than or equal to 5% of the peak to peak amplitude of the transmit signal. The bias signal 660 is maintained at a "high" level for a substantial majority of the duration of the transmit signal (e.g., continuously or over 90% of the 200 µs duration).

The bias signal 660 is merged with the transmit signal 650 to form a biased transmit signal 670 that includes a first biased polarity segment 672 and a second biased polarity segment 674. The bias transmit signal 670 is shifted to have a quiescent level 676 that is shifted in the same direction as the poling direction by the amount corresponding to the amplitude of the bias signal 660. The biased transmit signal 670 is shifted in the direction of the poling direction but still includes both of positive and negative voltages over a transmit cycle. In this example, the first biased polarity segment 672 may extend in the poling direction, while the second biased polarity segment 674 may extend in the non-poling direction. The first biased polarity segment 672 has a peak amplitude corresponding to the sum of the amplitude of the peak positive transmit pulse and the amplitude of the bias signal (e.g., $+V_T+V_B$), while the second biased polarity segment 674 has a peak amplitude corresponding to the difference of the amplitude of the peak negative transmit pulse and the amplitude of the bias signal (e.g., $-V_T+V_B$). In the present example, the poling direction is in the positive direction and therefore, the first biased polarity segment 672 refers collectively to any/all portions of the biased transmit signal 670 that have a positive voltage, while the second biased polarity segment 674 refers collectively to any/all portions of the transmit signal 650 that have a negative voltage. Optionally, the first biased polarity segment 672 may extend in the non-poling direction, while the second biased polarity segment 674 may extend in the poling direction. The sequence of the first and second biased polarity segments 672 and 674 do not matter. The bias signal 660 may be limited to the length of the transmit pulse 656 or the bias signal 660 may extend for the entire pulse repetition time. For example, the bias signal 660 may be active during the entire transmit/receive period, or the bias signal 660 may be any length in-between.

The bias transmit signal 670 substantially eliminates the de-poling in the transducer elements by shifting the transmit signal in the poling direction by the amount corresponding to the level of the bias signal. The shift corresponding to the bias signal is defined in terms of a ratio or relation to the voltage applied during transmit operations. In accordance with at least certain embodiments, the shift corresponding to the bias signal is maintained in a range of 2.5V to 10V, and more preferably in a range of 4-9V, and even more preferably in a range of 5-6V. For transmit operations that use a peak voltage of up to 30V, the bias signal may be up to 25% (and more preferably at or below 15%, and even more preferably at or below 10%) of the peak voltage of the transmit signal generated during a transmit cycle. For example, when the transmit voltage is varied between +/−60 V, the DC bias voltage was maintained at or below +/−9V, and more preferably +/−6 V. By maintaining the level of the bias signal at a level between 2.5V to 10V, and more preferably 4-9V and even more preferably 5-6V, embodiments herein form a biased transmit signal having first and second biased polarity segments that substantially maintain amplitudes of the original transmit signal extending in the poling direction and in the non-poling direction, but shifted a small percentage in the poling direction. The foregoing bias transmit signal stabilizes the electrical dipole orientation of the composition within the transducer elements and thus avoid (or at least substantially diminish) depoling effects, while allowing implementation utilizing low voltage biasing circuitry.

Further, the bias signal 662 is defined to have a pulse width that is relatively long as compared to a length of the poling segments (e.g., 652, 654) of the transmit signal, thereby further stabilizing the electrical dipole orientation of the transducer material. For example, the DC bias signal may be maintained continuously throughout an entire transmit and receive cycle and/or maintained for a substantial majority of the transmit and receive cycle (e.g., 90% or more).

Figure 7:
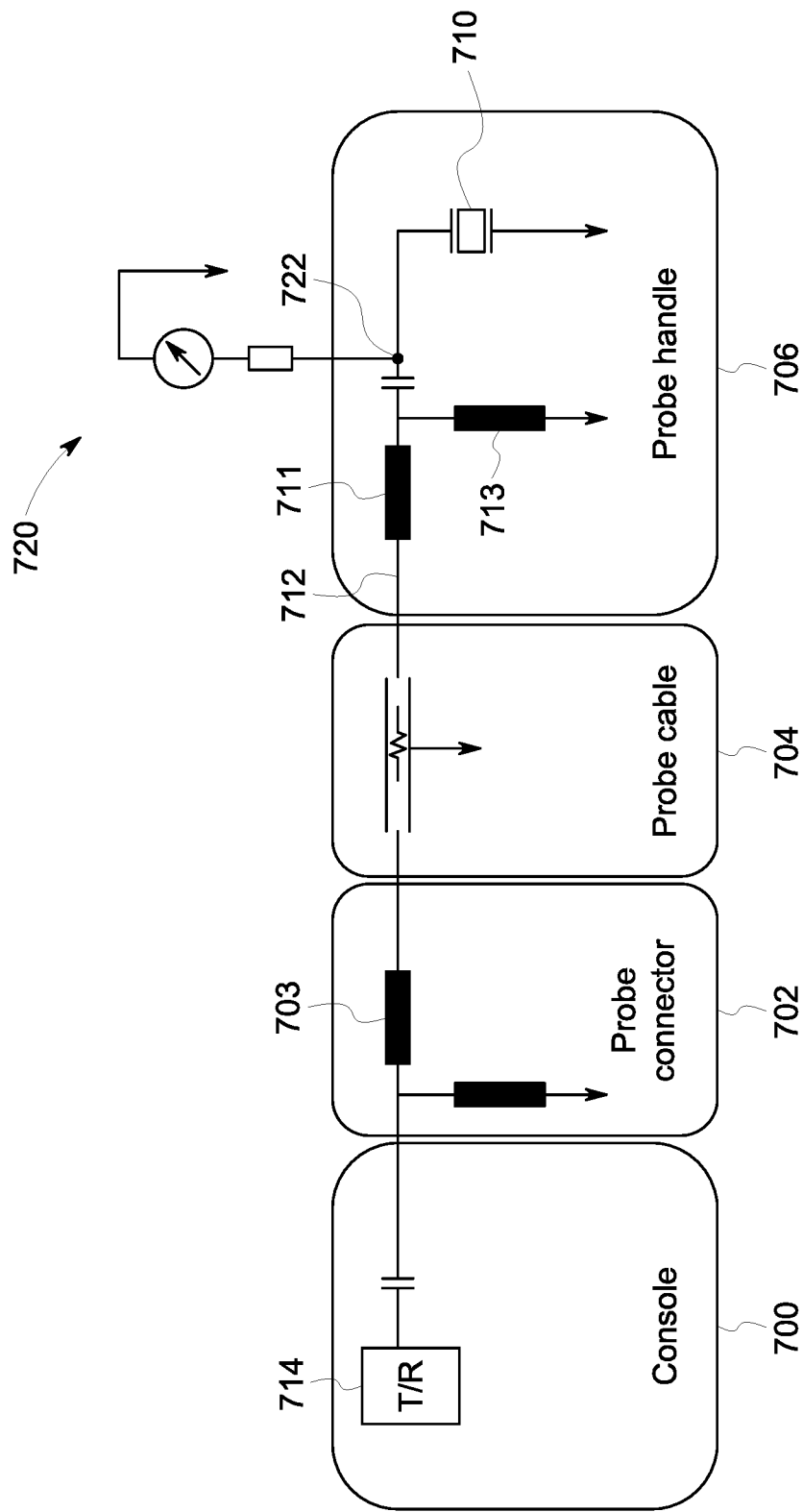
FIG. 7 illustrates a block diagram of an ultrasound system including a DC bias circuit implemented in accordance with embodiments herein.

FIG. 7 illustrates a block diagram of an ultrasound system including a DC bias circuit implemented in accordance with embodiments herein. The ultrasound system includes a console 700 that is connected to a probe connector 702. The console 700 may include all or a portion of the components described and illustrated in connection with one or more of FIGS. 1-4. The probe connector 702 is provided on a proximal end of a probe cable 704. A distal end of the probe cable 704 is connected to a probe 706. A line 712 electrically connects a transducer element 710 to corresponding contacts (not shown) in the probe connector 702. An inductor combination 711, 713 is provided within the probe 706. An inductor 703, within the probe connector 702, is also provided along line 712. The probe cable 704 is connected at the probe connector 702 to a transmit/receive (T/R) circuit 714 within the console 700.

During transmit operations, the T/R circuit 714 delivers a transmit signal to cause the transducer element 710 to transmit ultrasound signals. During receive operations, the T/R circuit 714 records return "echo" signals along line 712 corresponding to ultrasound echo waves sensed at the transducer element 710. A biasing circuit 720 is connected at node 722 within the probe 706. The biasing circuit 720 is configured to introduce a bias signal, such as a DC bias voltage, onto the line 712. The bias signal is superimposed at node 722 onto the transmit signal generated by the transmit/receive circuit 714. The configuration of FIG. 7 allows the biasing circuit 720 to be implemented within each individual probe 706, thereby avoiding any need for modification to conventional consoles for ultrasound systems. Furthermore, the configuration of FIG. 7 is possible if parallel inductors between transmit/receive line and ground are used in probe handle or probe connector.

Optionally, the embodiment of FIG. 7 (as well as other embodiments herein) may be implemented in connection with wireless probes where the bias circuitry is implemented within the probe handle.

Figure 8:
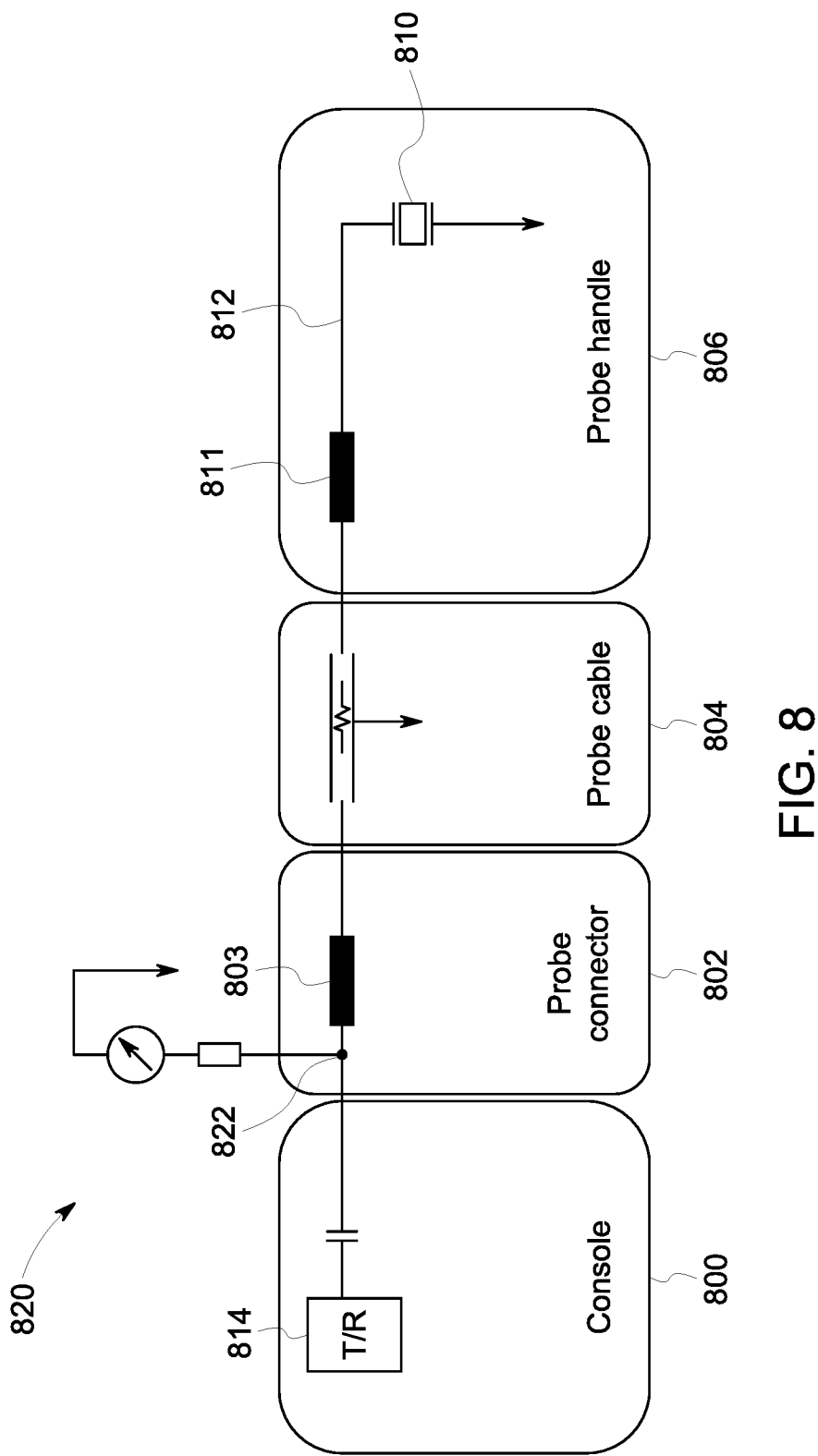
FIG. 8 illustrates a block diagram of an ultrasound system including a DC bias circuit implemented in accordance with embodiments herein.

FIG. 8 illustrates a block diagram of an ultrasound system including a DC bias circuit implemeneted in accordance with embodiments herein. The ultrasound system includes a console 800 that is connected to a probe connector 802. The console 800 may include all or a portion of the components described and illustrated in connection with one or more of FIGS. 1-4. The probe connector 802 is provided on a proximal end of a probe cable 804. A distal end of the probe cable 804 is connected to a probe 806. A line 812 electrically connects a transducer element 810 to corresponding contacts (not shown) in the probe connector 802. An inductor 811 is provided within the probe 806, and an inductor 803 is provided within the probe connector 802 along line 812. The probe cable 804 is connected at the probe connector 802 to a transmit/receive (T/R) circuit 814 within the console 800.

During transmit operations, the T/R circuit 814 delivers a transmit signal to cause the transducer element 810 to transmit ultrasound signals. During receive operations, the T/R circuit 814 records return "echo" signals along line 812 corresponding to ultrasound echo waves sensed at the transducer element 810. A biasing circuit 820 is connected at node 822 within the probe connector 802. The biasing circuit 820 is configured to introduce a bias signal, such as a DC bias voltage, onto the line 812. The bias signal is superimposed at node 822 onto the transmit and receive line. The configuration of FIG. 8 allows the biasing circuit 820 to be implemented within the probe connector 802, thereby avoiding any need for modification to conventional consoles for ultrasound systems and potentially to an existing design for the internal components of the probe body.

Figure 9:
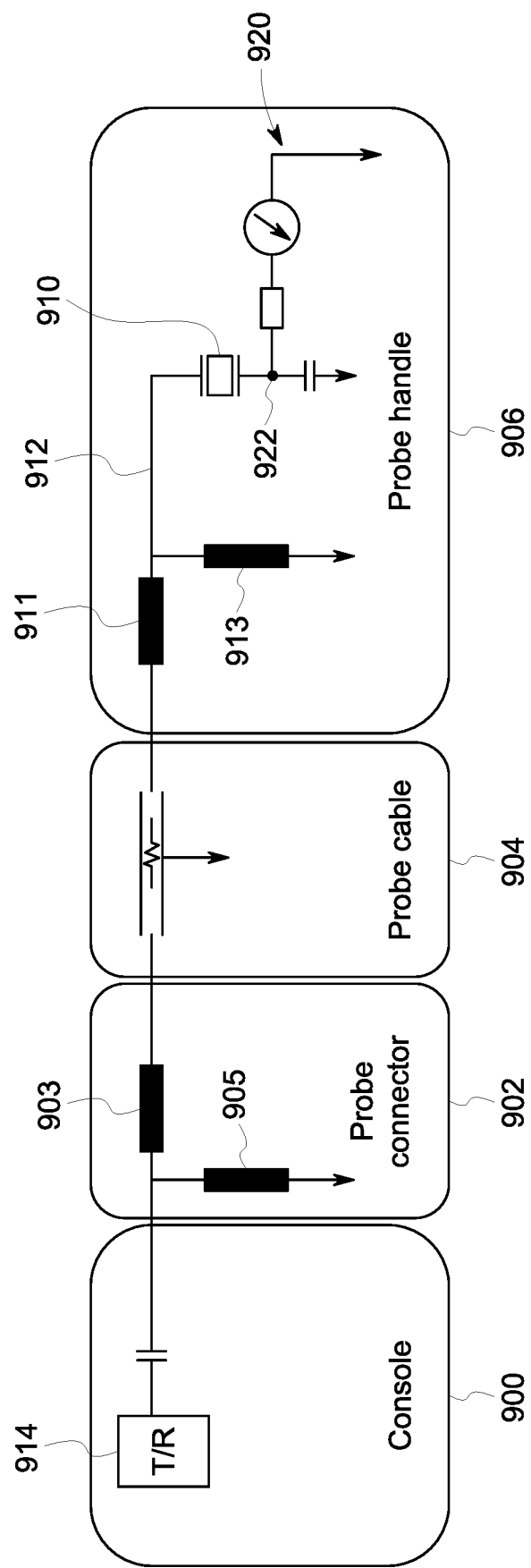
FIG. 9 illustrates a block diagram of an ultrasound system including a DC bias circuit implemented in accordance with embodiments herein.

FIG. 9 illustrates a block diagram of an ultrasound system including a DC bias circuit implemented in accordance with embodiments herein. The ultrasound system includes a console 900 that is connected to a probe connector 902. The console 900 may include all or a portion of the components described and illustrated in connection with one or more of FIGS. 1-4. The probe connector 902 is provided on a proximal end of a probe cable 904. A distal end of the probe cable 904 is connected to a probe 906. A line 912 electrically connects a transducer element 910 to corresponding contacts (not shown) in the probe connector 902. An inductor combination 911, 913 is provided within the probe 906, and an inductor combination 903, 905 is provided within the probe connector 902. The probe cable 904 is connected at the probe connector 902 to a transmit/receive (T/R) circuit 914 within the console 900.

During transmit operations, the T/R circuit 914 delivers a transmit signal to cause the transducer element 910 to transmit ultrasound signals. During receive operations, the T/R circuit 914 records return "echo" signals along line 912 corresponding to ultrasound echo waves sensed at the transducer element 910. A biasing circuit 920 is connected at node 922 within the probe 906 between the transducer element 910 and ground. The biasing circuit 920 is configured to introduce a bias signal, such as a DC bias voltage, onto the line 912. The ground potential of the transducer is shifted by the DC-bias. The bias signal is superimposed at node 922 onto the ground voltage level. The configuration of FIG. 9 allows the biasing circuit 920 to be implemented within the probe connector 902, thereby avoiding any need for modification to conventional consoles for ultrasound systems. Furthermore, the configuration of FIG. 9 is possible if parallel inductors between transmit/receive line and ground are used in probe handle or probe connector. The ground potential of the transducer is often connected to many or all elements in parallel. Therefore, the configuration of FIG. 9 does not require a modification of each transmit/receive line and is easier to implement.

Optionally, the embodiment of FIG. 9 (as well as other embodiments herein) may be implemented in connection with wireless probes where the bias circuitry is implemented within the probe handle.

From the foregoing examples in FIGS. 6A-9, it is seen that the biasing voltage can be generated and introduced after the AC coupled beamformer, at the probe connector, within the probe upstream of the transducer element, within the probe downstream of the transducer element as well as elsewhere. In the embodiments of FIGS. 7 and 8, the bias signal is applied to each line that carries a corresponding transmit signal. In the embodiment of FIG. 9, the ground connection can be DC decoupled on the transducer and the bias signal applied as an inverse voltage to the transducer ground.

In accordance with aspects herein, embodiments increase stability of depolarization. In accordance with aspects herein, embodiments enable a relatively low bias voltage to be utilized (<10V approximately <1 kV/cm) and does not necessarily lead to unipolar signals, but instead biased bipolar signals. In accordance with aspects herein, embodiments achieve a substantial increase in depolarization stability when biasing voltages are applied to binary SC materials (e.g., PMN-PT). In accordance with aspects herein, several unexpected results were found. First, it was unexpected to find that a low DC bias achieved the same or better depoling effects as substantially higher voltage bias signals for binary single crystal material (binary SC). Further, it was unexpected to find that a low voltage bias signal does work to some degree with ternary single crystal (ternary SC), but not as well as the low voltage bias signal works with binary single crystal material. Further, it was unexpected to find the low voltage bias signal stabilizes the weaker binary SC material to voltages equal or beyond the capability of ternary SC materials.

Tests were conducted to study the depoling effect exhibited by piezoelectric substrates formed from certain types of single crystal materials. The test analyzed different transducers. In connection with the test, various transducers were excited with different transmit patterns that were combined with bias signals having different voltage levels. Some of the test results are shown in the following Figures.

Figure 10:
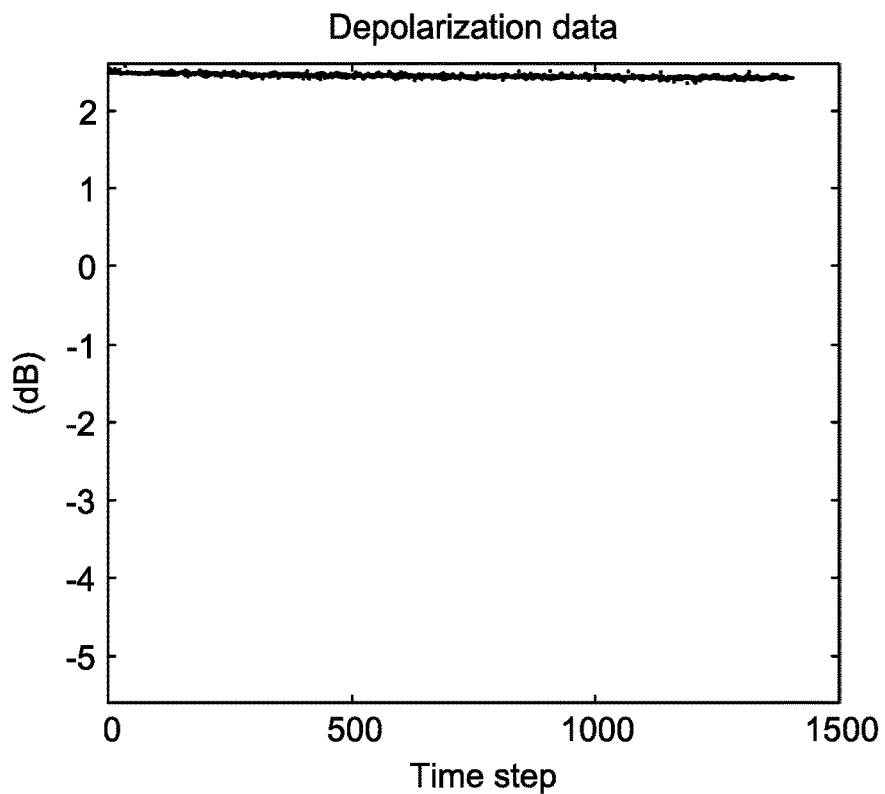
FIG. 10 illustrates the test with applied DC-bias results collected in connection with one type of transducer in accordance with embodiments herein.

FIG. 10 illustrates the test results collected in connection with one type of transducer that utilized binary single crystal materials, with sensitivity indicated in decibels along the vertical axis and a time of operation indicated along the horizontal axis. In connection with the measurement, the transducer elements were excited with a transmit signal having a desired pattern, along with a bias signal having a 5V DC steady-state amplitude. The transmit signal included one or more positive segments having a peak positive amplitude >60 V and one or more negative segments having a peak negative amplitude of >−60 V. When combining the bias signal with the transmit signal, the resulting biased transmit signal which shifted in the direction of the poling direction of the transducer elements by a 5V DC steady-state amplitude. The biased transmit signal was applied to the transducer elements for a total operating time of several hours. Periodically, throughout operation, a sensitivity of the transducer elements was measured to compare the ratio of the input and output power levels. As illustrated in FIG. 10, the sensitivity remained stable at between 2 dB and 3 dB over the hours of operation.

Figure 11:
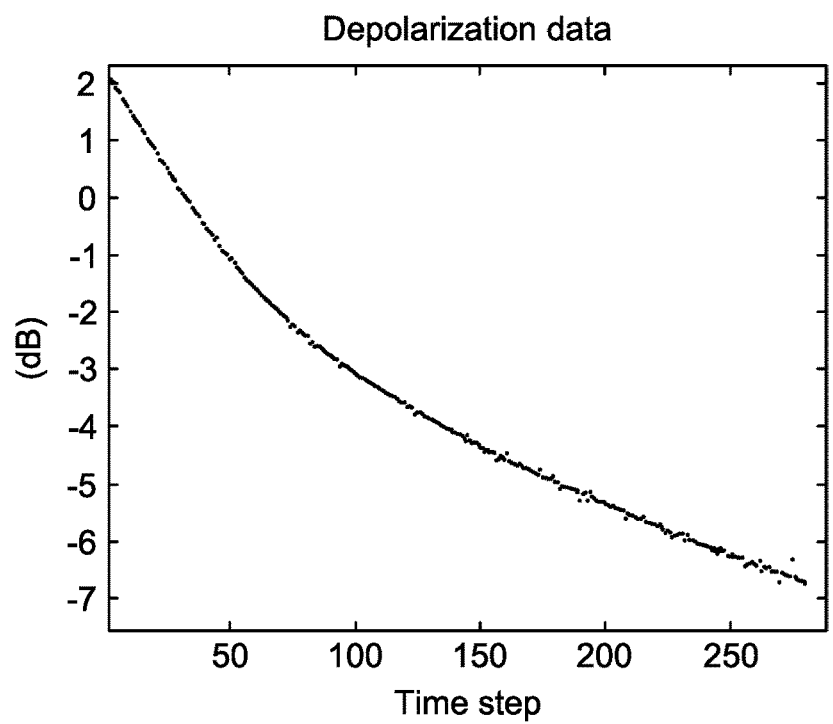
FIG. 11 illustrates the test results without DC-bias collected in connection with the same type of transducer as tested in connection with FIG. 10 in accordance with embodiments herein.

FIG. 11 illustrates the test results collected in connection with the same type of transducer as tested in connection with FIG. 10, with sensitivity indicated in decibels along the vertical axis and a time of operation indicated along the horizontal axis. In connection with the measurement, the transducer elements were excited with a transmit signal having the same transmit pattern as applied in connection with the test of FIG. 10, but with no bias signal (e.g., a bias signal was set to 0V) added to the transmit signal. The test results in FIG. 11 indicate the sensitivity of the transducer over the test period of operation when a non-biased transmit signal is applied alone. The transmit signal was applied to the transducer elements for a total operating time of several minutes. Periodically, throughout the minutes of operation, a sensitivity of the transducer elements was measured to compare the ratio of the input and output power levels. As illustrated in FIG. 11, the sensitivity dropped from an initial level at slightly less than 3 dB at a relatively sharp rate. In the first 10 minutes, the sensitivity had dropped to a −3 dB, at approximately 20 minutes, the sensitivity had dropped to −5 dB and at 30 minutes, the sensitivity was approaching a −7 dB.

From the foregoing tests of FIGS. 10 and 11, it is clear that application of a bias signal in a direction of the poling direction of the transducer elements stabilizes the transducer over a period of several hours of operation.

Figure 12:
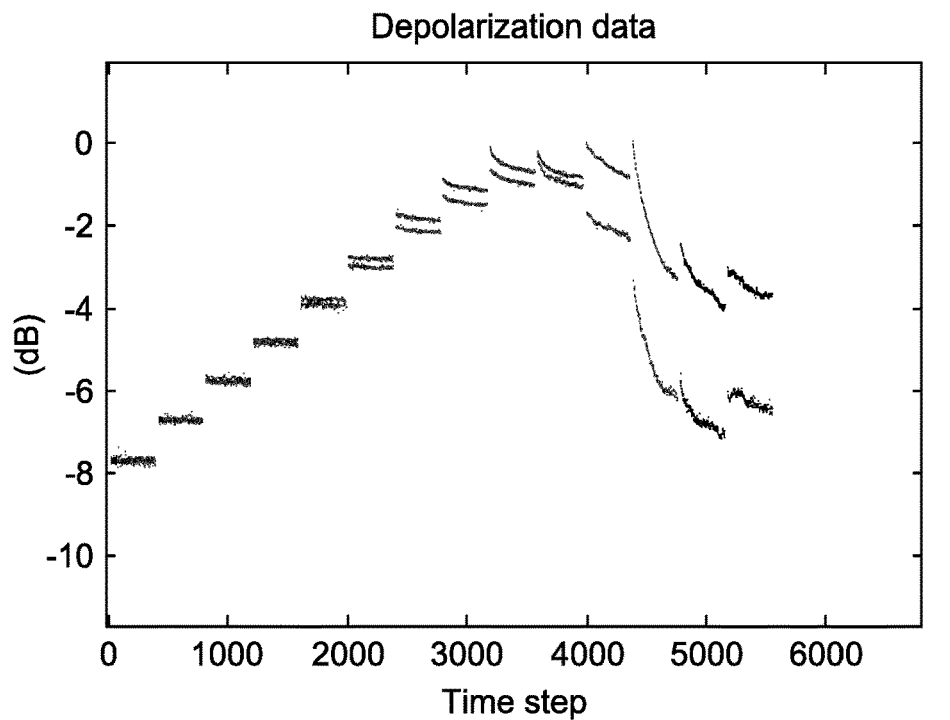
FIG. 12 illustrates test results without DC-bias collected in connection with one type of transducer in accordance with embodiments herein.

FIG. 12 illustrates test results collected in connection with one type of transducer that utilized binary single crystal materials, with sensitivity indicated in decibels along the vertical axis and a time of operation indicated along the horizontal axis. During the test, the transducer was excited with a transmit signal that utilized harmonic pulse inversion, but with no bias signal (e.g., a bias signal was set to 0 V) added to the transmit signal. A series of horizontal measurement lines are illustrated, each of which corresponds to a few minutes of measurement cycle. During each measurement cycle, a particular voltage level was utilized for the transmit signal, with different voltage levels applied during different measurement cycles. For example, the transmit voltage was started at approximately 25 V and was increased in steps during each measurement cycle until reaching 120 V. The sensitivity measurements during the first 2-3 hours remained relatively constant. However, after 3-4 hours of operation, the sensitivity begins to drop during the measurement cycles.

Figure 13:
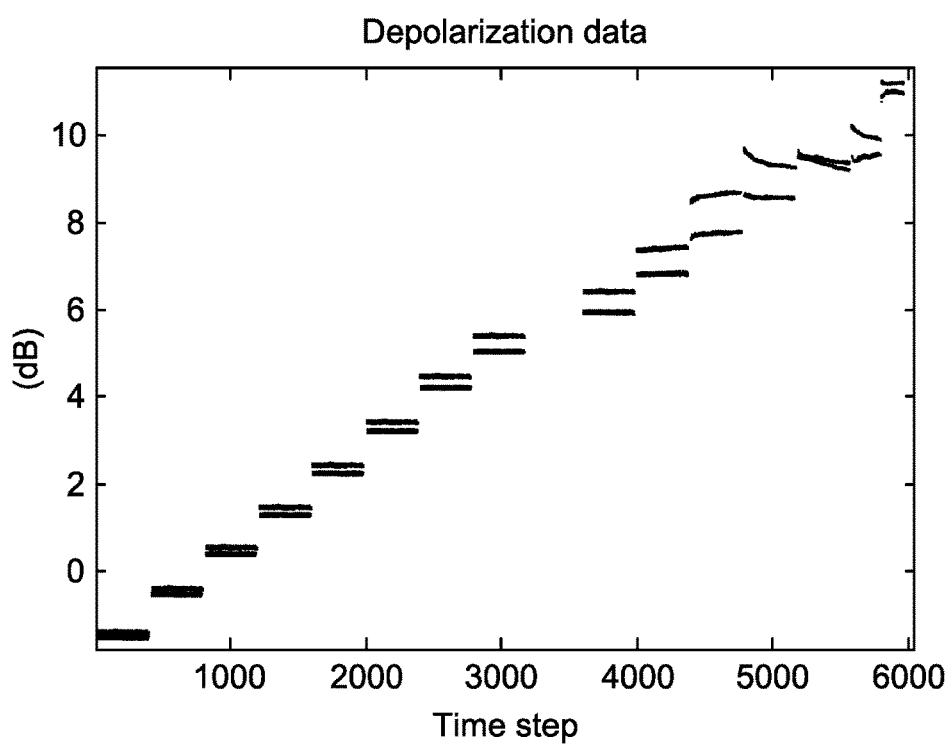
FIG. 13 illustrates test results with applied DC-bias collected in connection with the same type of transducer as used in the test results for FIG. 12 in accordance with embodiments herein.

FIG. 13 illustrates test results collected in connection with the same type of transducer as used in the test results for FIG. 12, with sensitivity indicated in decibels along the vertical axis and a time of operation indicated along the horizontal axis. During the test, the transducer was excited with the same type of transmit signal and with the same transmit voltage steps as utilized in FIG. 12, along with a bias signal having a 10 V DC steady-state amplitude. A series of horizontal measurement lines are illustrated, each of which corresponds to a measurement cycle of several minutes. During each measurement cycle, a particular corresponding voltage level was utilized for the transmit signal, with different voltage levels applied during different measurement cycles.

From the test results of FIGS. 12-13, it can be seen that the application of a bias signal in a direction of the poling direction of the transducer elements stabilizes the transducer elements at higher transmit voltages. For example, up to 6 dB higher transmit voltage may be utilized without the transducer elements exhibiting the depoling effects.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An ultrasound system, comprising:
a transducer with piezoelectric transducer elements formed from a slab of piezoelectric material and polarized in a poling direction;
a transmit circuit configured to generate a transmit signal having at least first and second polarity segments, the first and second polarity segments having corresponding first and second peak amplitudes; and
a bias generator configured to generate a bias signal in a direction of the poling direction, wherein the bias signal is combined with the transmit signal to form a biased transmit signal that is shifted in the direction of the poling direction and includes both of positive and negative voltages over a transmit cycle.

2. The ultrasound system of claim 1, wherein the piezoelectric transducer elements are formed from a single crystal material polarized in the poling direction.

3. The ultrasound system of claim 2, wherein the single crystal material represents a binary single crystal material.

4. The ultrasound system of claim 1, wherein the bias signal is a DC voltage that is applied continuously.

5. The ultrasound system of claim 1, wherein the bias generator is configured to generate the bias signal to have a steady-state voltage of between 2.5V and 10V.

6. The ultrasound system of claim 1, wherein the bias generator is configured to generate the bias signal to have a steady-state voltage of up to 15% of at least one of the first or second peak amplitudes of the transmit signal.

7. The ultrasound system of claim 1, wherein the transmit signal includes a series of pulses that repeat, the pulses having a predetermined pulse width to provide an active transmit signal for up to 5% of the transmit cycle, the bias generator configured to apply the bias signal during 90% or more of the transmit cycle.

8. The ultrasound system of claim 1, wherein the transmit signal includes a series of pulses that repeat, the pulses having a predetermined pulse width to provide an active transmit signal for up to 5% of the transmit cycle, the bias generator configured to apply the bias signal continuously during the transmit cycle.

9. The ultrasound system of claim 1, further comprising a probe coupled to a distal end of a probe cable, the probe cable including a probe connector at a proximal end of the probe cable, the probe connector configured to be connected to an ultrasound console, the bias generator located within the ultrasound console downstream of the bipolar transmit circuit and before the probe connector.

10. The ultrasound system of claim 1, further comprising a probe, the bias generator located in the probe.

11. An ultrasound probe, comprising:
a transducer with piezoelectric transducer elements formed from a slab of piezoelectric material and polarized in a poling direction;
a probe connector and a transmit line extending from the probe connector to the transducer, the transmit line configured to convey a transmit signal having at least first and second polarity segments, the first and second polarity segments having corresponding first and second peak amplitudes; and
a bias generator configured to generate a bias signal in a direction of the poling direction, wherein the bias signal is combined with the transmit signal to form a biased transmit signal that is shifted in the direction of the poling direction and includes both of positive and negative voltages over a transmit cycle.

12. The ultrasound probe of claim 11, wherein the piezoelectric transducer elements are formed from a single crystal material polarized in the poling direction.

13. The ultrasound probe of claim 11, wherein the bias generator is configured to generate the bias signal to have a steady-state voltage of between 2.5V and 10V.

14. A method, comprising:
utilizing a transducer to transmit ultrasound signals and receive echo ultrasound signals from a region of interest, the transducer including piezoelectric transducer elements formed from a slab of piezoelectric material and polarized in a poling direction;
generating a transmit signal having at least first and second polarity segments, the first and second polarity segments having corresponding first and second peak amplitudes; and
generating a bias signal in a direction of the poling direction; and
combining the bias signal with the transmit signal to form a biased transmit signal that is shifted in the direction of the poling direction and includes both of positive and negative voltages over a transmit cycle.

15. The method of claim 14, further comprising at least one of:
generating the bias signal to have a steady-state voltage of up to 10V;
generating the bias signal to have a steady-state voltage of up to 6V;
generating the bias signal to have a steady-state voltage of up to 15% of at least one of the first or second peak amplitudes of the transmit signal; or
continuously applying the bias signal during 90% or more of the transmit cycle.

16. The ultrasound system of claim 1, wherein the biased transmit signal includes a first biased polarity segment that extends in the poling direction and a second biased polarity segment that extends in the non-poling direction.

17. The ultrasound system of claim 1, wherein the first polarity segment of the transmit signal has a positive voltage and the second polarity segment of the transmit signal has a negative voltage, the biased transmit signal having a first biased polarity segment and a second biased polarity segment, the first biased polarity segment having a positive voltage that is shifted relative to the positive voltage of the first polarity segment, the second biased polarity segment having a negative voltage that is shifted relative to the negative voltage of the second polarity segment.

18. The ultrasound system of claim 1, wherein the slab of piezoelectric material has a proximal surface and a distal surface, and the proximal and distal surfaces are spaced apart from one another by a thickness of the slab, wherein the thickness of the slab is selected based on a wavelength of sound in the piezoelectric material for a desired center frequency of a useful bandwidth.

19. The ultrasound system of claim 18, wherein the thickness of the slab is approximately ½ or ¼ of the wavelength of sound in the piezoelectric material for the desired center frequency of the useful bandwidth.

20. The ultrasound system of claim 1, wherein the slab of piezoelectric material includes multiple kerfs that extend from a proximal surface of the slab through the piezoelectrical material towards a distal surface of the slab, the kerfs separating the piezoelectric transducer elements.

* * * * *